United States Patent [19]

Carduck et al.

[11] 4,335,144
[45] Jun. 15, 1982

[54] PREPARATION OF POROUS ACTIVE YEAST GRANULES

[75] Inventors: Franz-Josef Carduck, Haan; Dietrich Kloetzer, Dusseldorf; Gerard Veldman, Brüeggen, all of Fed. Rep. of Germany

[73] Assignee: Deutsche Hefewerke GmbH, Hamburg-Wandsbek, Fed. Rep. of Germany

[21] Appl. No.: 226,146

[22] Filed: Jan. 19, 1981

Related U.S. Application Data

[63] Continuation-in-part of Ser. No. 21,781, Mar. 19, 1979, abandoned.

[51] Int. Cl.$^3$ .................. C12C 11/18; C12C 11/32
[52] U.S. Cl. .................................. 426/62; 426/60; 426/445; 426/448; 435/256; 435/260
[58] Field of Search ............... 426/60, 62, 445, 446, 426/448, 656; 435/256, 260

[56] References Cited

U.S. PATENT DOCUMENTS 2,710,810 10/1955 Sfrashun ..................... 435/260 X
2,921,854 1/1960 Parker ......................... 426/62 X
3,843,800 10/1974 Langejan et al. ............. 426/62 X

FOREIGN PATENT DOCUMENTS 2637601 2/1977 Fed. Rep. of Germany ....... 426/62

*Primary Examiner*—David M. Naff
*Attorney, Agent, or Firm*—Hammond & Littell, Weissenberger and Muserlian

[57] ABSTRACT

Porous granules of active yeast are produced by mixing moist yeast having a solids content of 30% to 40% with a gas in an amount of 0.2 to 2.0 times the volume of the yeast, extruding the resultant mixture at a pressure of from 1 to 10 atmospheres through orifices having a length to diameter ratio of about 1:1 to 4:1 and allowing escape of gas from the interior of the resultant extrudate to form pores communicating with the surface to produce porous granules of active yeast. The granules may be dried to produce active dry yeast granules having a total surface area formed by the outside surface plus the interior surface of the granules of at least 1.5 times the total area of the outside surface of the granules. The active dry yeast granules have good vitality and are capable of rapid rehydration and regeneration.

10 Claims, 4 Drawing Figures

PREPARATION OF POROUS ACTIVE YEAST GRANULES

REFERENCE TO PRIOR APPLICATIONS

This application is a continuation-in-part of Ser. No. 021,781, filed Mar. 19, 1979 now abandoned.

FIELD OF THE INVENTION

The present invention relates to the production of active dried granulated yeast from cultures and, more particularly, to the high vitality yeast granules so prepared.

BACKGROUND OF THE INVENTION

Yeasts have been marketed in the form of moist cultures or compressed cakes because it has been found that improper dehydration or even drying outside of very narrow limits can cause the yeast to suffer a shock and thereby lose some or all of its life force or vitality. In order to prevent such shocks, until now, it has been the practice to dry the yeasts at relatively low temperatures and at relatively high humidity. This required the use of rack and tray driers or continuous belt driers and required long drying times in order to keep the moist yeast alive until sufficiently dehydrated to reach the dormant stage at which there is a suspension of the yeast metabolism. Such dormant yeast can be regenerated.

Apart from requiring complex and expensive operating and control apparatus, slow drying also has the disadvantage of reducing the vitality of the yeast. The yeast, while still moist, during the lengthy drying procedure, lacking other sources of nutriment, metabolizes its stored nutriments as well as its own substance. Upon rehydration, the regenerated yeasts, are found to have lost a substantial portion of the original vigor and vitality.

The terms, vigor and vitality, as used herein, refer to the qualities of growth and reproduction, respectively, of the yeast.

Some improvement has been attained by dehydrating the yeast in two drying stages: a first stage, preliminary drying in moist air (relative humidity of 75 to 80%) and, thereafter, a final drying stage with dry air. This process is described in German Pat. No. 857 784 and is energy inefficient, requires inordinately long drying times and expensive apparatus.

Also disclosed in German Pat. No. 857 784 is an apparatus by which moist yeast can be granulated before drying. The granules are there formed by forcing the moist yeast through an apertured metal plate and subdividing the resultant strands into short sections by cutting elements moving behind the apertured plate. Since the cutting elements have relatively smooth surfaces and sharp cutting edges, provision is made in this prior art for rounding off the resulting strand sections by rolling them in a granulating drum before or during the initial drying stage. Since the resulting rolled yeast granules are only surface treated, the drying still requires the aforementioned two-stage process of a preliminary moist-air drying and the subsequent dry-air drying.

U.S. Pat. No. 2,921,854 describes a method of aggregating powdered yeast having sizes from 5 to 20 microns to give particles substantially retained on a 60-mesh sieve. An agglomerated powdered dry yeast having a diameter of a little greater than 0.25 mm is obtained.

U.S. Pat. No. 3,843,800 describes a process for drying compressed yeast granules where the yeast cells are held within a temperature range of 20° C. to 50° C. in a fluidized bed type of dryer at atmospheric pressure. This compressed yeast is extruded to form strands. After mixing the dough for 6 minutes at 28° C., complete rehydration occurs.

DE-OS No. 26 37 601 describes a process for drying of an extrudate granule from a low pressure extruder where after drying to a solids content of about 70%, the semi-dried aggregate is ground to give a powder which is then further dried.

U.S. Pat. No. 2,710,810 relates to a process of vacuum dehydration of microbial liquid cultures. Under these conditions, the concentrate expands and the final product is also in an expanded state. This expansion is caused by the entrapment of a multitude of small steam bubbles throughout the mass as a foaming operation. Fast rehydration occurs by this process. It is suggested that this expansion can be enhanced by introduction of an inert gas into the liquid concentrate. The example employs a liquid concentrate containing 25% solids to which is added corn syrup solids to give a 50% solids concentrate. This concentrate was vacuum dehydrated at a temperature of from 200° F. to 80° F. and expanded 16 times.

Before use, the dried yeast granules must be rehydrated by moisture in order to regenerate the now passive or dormant yeast cells. During this regeneration by rehydration, the individual yeast cells absorb water, and regain their normal appearance. This regeneration and moisture reabsorption, however, takes place over a finite time period. During the initial phases of the regeneration period there is the danger of malabsorption leading to "bleeding" or exudation of the cell contents of some of the cells thus damaging or even killing the entire yeast culture. To minimize this exudation phenomena caused by the rupture of the cell walls, it is usual to rehydrate the dried yeast granules by suspending them in water at temperatures in the range of 30° to 40° C. Within the stated temperature range, the hydration and regeneration take place with a minimum malabsorption, cell wall disruption, and a prevention of the reduction of the vitality of the yeast occurs by exposure to too high a temperature.

During the rehydration of the dried yeasts, granulated according to the previous procedures, difficulties have been noted such as uneven regeneration of yeast cells in each granule. Cells on the exposed outer surface of the granules rehydrate and swell and thus hinder the penetration of the moistures to the dormant yeast cells at the interior portions of the granule. Accordingly, it is noted that the dried yeast granules of the prior art take a long time to regenerate and, further, because of this time span, the danger of ruptured cell walls is increased with its resulting losses in vitality and vigor of the regenerated yeast.

OBJECTS OF THE INVENTION

It is an object of this invention to provide a method for the efficient production of active granulated dried yeast.

It is a further object of this invention to provide a method for the production of active dried yeast having good vitality and which is capable of rapid rehydration and regeneration.

It is another object of this invention to provide a method for the production of a vigorous dried yeast in the form of porous granules.

These and other objects of the invention will become more apparent as the description thereof proceeds.

THE DRAWINGS

THE INVENTION

Figure 1:
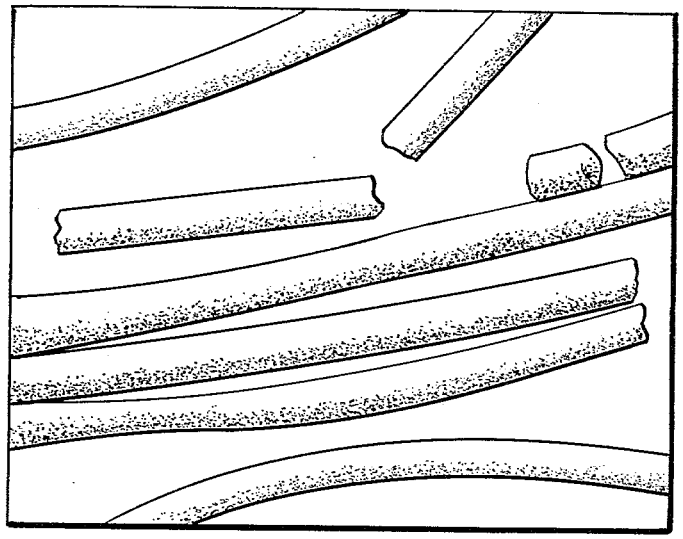
FIG. 1 shows extruded strands of compressed yeast according to the prior art.

These and additional objects are achieved by the discovery of a certain novel form of dried yeast granules and a method for their preparation. The dried yeast granules of this invention are provided in a porous form having pores extending into and through the body of the granules. As a result of this porous structure, the compressed moist yeast, from which the novel granules are formed, can be rapidly dehydrated to the dormant condition of the yeast without sapping the vigor and vitality of the yeast. In addition, the pores permit the rapid rehydration and regeneration of the dormant yeast by permitting ready and rapid access of the regeneration medium, water, to the innermost parts of the granules. The result of such rapid rehydration and regeneration is a vigorous yeast culture with minimal "bleeding" or cell-wall damage. The porosity of the dried yeast granules of this invention should provide a mean surface area of the individual granules at least 1.5 times the dimensional surface area, but, preferably, should be above about 2 to 10 times the dimensional surface area. Such extended surface areas result from the interior surfaces exposed by communicating pores and passages extending into the interior of the granules.

The novel dried yeast granules of the invention may easily be prepared by the process aspects of the invention which is based upon steps which comprise the admixture and incorporation into the moist yeast of a gas, compressing the resultant plastic yeast-gas mass, subdividing the compressed mass into granules, releasing the confining pressure on the granules to permit escape of the confined gas from the interior of the granules, thus forming interior pores in said granules communicating with the surface, and then drying the resultant porous granules.

DETAILED DESCRIPTION OF THE INVENTION

The dried yeast granules of this invention are in the form of porous discrete particles. As a result of the presence of the pores extending from the interior of the particles to the surface of the particles, the external surface of the granular particles is quite rough in microscopic appearance. This is in contrast to the smooth appearance of the granules obtained by the prior art processes hereinabove described. The porosity of the granules of this invention permits rapid dehydration of the moist yeast. The pores provide avenues for the rapid diffusion and conduction of the moisture through the resultant passages from the yeast cells in the interior of the granules. Because of the ready passage of the moisture, the yeast cells are rapidly rendered into their dormant state before their vigor and vitality are reduced by unnourished metabolism as often occurs during the prolonged two-stage drying as required by the prior art.

A convenient measure of the porosity of the granules of the invention is that before dehydration they should have total extended surface areas at least twice the surface areas as defined by the dimensions of the individual granules. During drying, of course, due to the shrinkage of the yeast cells, the extended surface areas increase greatly. Preferably, the extended surface areas of the dried yeast granules should be at least 1.5 to twenty times the dimensional areas of the granules, with an optimum range of about 2 to about 10 times the dimensional area.

The process aspects of this invention are preferably carried out in an extrusion apparatus wherein the moist yeast, freed from the excess culture media and having a solids content of about 30% to 40%, is introduced into the extruder chamber. Gas such as air, $CO_2$ or $N_2$ is introduced into the chamber and mixed with the moist yeast until the gas is sufficiently and uniformly incorporated into the yeast to form a uniform mass. The incorporation of the gas into the mass may be assisted by the addition of food-safe emulsifiers to the mass. The uniform mass of the yeast solids and the gas is then compressed by the extruder and extruded therefrom in the form of strands. Upon extrusion, the confined gas from the interior of the strands is freed and escapes to the surface, thus forming communicating pores from the interior to the surface. As a result of the pore-formation, the strength of the strands is weakened and the strands subdivide into individual porous granules.

As set forth above, an extrusion apparatus is preferred for the preparation of the granules of this invention but any apparatus that affords the serial steps of incorporating a gas into the moist yeast to form a mass, permits compression of the mass, followed by subdivision of the mass, and release of the gas from the subdivided mass to render it porous and in granular form, is also acceptable.

When an extrusion apparatus is employed, preferably it is a mixer extruder such as the "Continua", a two screw mixing and kneading extruder sold by Werner and Pfleiderer, Stuttgart, Germany. The extruder is described by Millauer in "Maschinemarkt", January 1973. Another type of extrusion apparatus which can be employed is a simple screw degassing extruder utilizing the Hartig vent system, where compressed air is injected in the vent at a pressure less than the compression pressure on each side of the vent. Such an extruder is disclosed in "Kunststoff-Handbuch", Vol. VI, pages 296–297 (1966), published by Carl Hanser Verlag, Munich, Germany.

The porosity of the mass after release of the pressure is a factor of the volume of gas present in the moist mass and the pressure of compression. The gas volume should be from 0.2 to 2.0 times the volume of the moist yeast mass and the pressure of compression should be from 1 to 10 atmospheres.

The granules resulting from the process aspects of the invention are initially in active moist form. To furnish yeast in the dormant form as commercially required for extended storage, these moist granules are dried. As a result of the high porosity of the granules of this invention, very rapid drying methods can be used without comprising the product. Among such rapid drying methods are fluidized-bed drying or counter current drying towers.

As a result of the increase of the surface area and the porosity of the extruded particles of moist yeast, granules of active dry baking yeast with a 94 to 97% dry solids content can easily be obtained by five to ten minutes of drying at nondestructive temperatures, for example, at 30° to 40° C., preferably, in a fluidized bed drier.

Such granular dried yeast, according to this invention, in dormant form, can be almost instantly regenerated for bakery use by the mere addition of warm water. This is in contrast to the granular yeasts of the prior art which require soaking and agitation to revive and, often, at only a fractional value of the strength of the initial moist yeast.

Thus, the yeast of this invention is dried in a simpler and more rapid manner than was possible hitherto, but also is in a condition where rapid regeneration or rehydration takes place. As a result of the rapid drying, the vitality of the yeast is maintained. Its condition for rapid regeneration prevents losses in vigor of the rehydrated yeast cells.

A further advantage of the process embodying the present invention is that due to the appreciable porosity, extending into the interior of the extruded particles of moist yeast as a result of the incorporation and release of the gas, the strands of moist yeast emerging from the extruder crumble into granules without recourse to "chopping" devices as is required according to the prior-art extrusion procedures.

As the gas to be admixed and incorporated into the body of the moist yeast and then compresssed therewith, any gas which is physiologically harmless to the yeast can be employed in the various suitable variants of the process of this invention. Air has been found to be an excellent and inexpensive gas for this step of the invention.

A preferred apparatus for performance of the process according to this invention is a twin screw mixer extruder comprising a confining chamber having apertured plates in which the apertures are fitted with nozzles.

The ratio of length to diameter of the extrusion nozzles may be from 1:1 to 4:1, preferably, about 2:1. Such a ratio range insures proper porosity of the particles and extension of the pores, formed by the released gas, through the body of the granular particles. In such extrusion apparatus the strands may be extruded at a linear rate of substantially 0.2 to 5 meters per second, preferably, between one and two meters per second.

Additionally, while not necessary, certain benefits in the ease in which the gas is incorporated into the moist yeast to form the compressible mass have been noted when common emulsifiers or wetting agents, such as are used in the food industry, are added to the moist yeast or to the mass prior to the compression step, such as forcing the mass through the extruder nozzles. Suitable emulsifiers or wetting agents, which are preferably used in amounts of from 0.5 to 5 percent, advantageously 1 to 2 percent, based on dry matter, are esters of saturated fatty acids, such as fatty acid esters of sorbitan, e.g., sorbitan monolaurate, monopalmitate, monostearate or mono-oleate; fatty acid esters of glycerol, e.g., glyceryl monostearate, a distearate or monopalmitate; fatty acid esters of propylene glycol, e.g., propylene glycol monostearate; or mixtures of two or more of the above-mentioned compounds.

Figure 2:
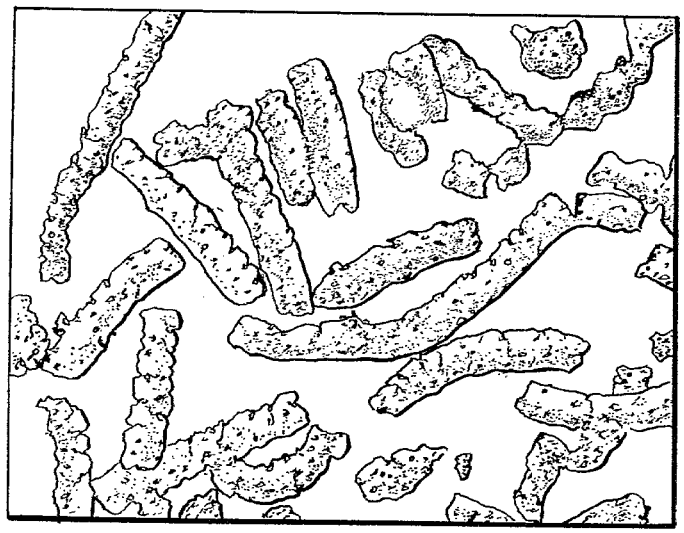
FIG. 2 shows extruded strands of compressed yeast according to the invention with gas incorporated therein.

The influence of gas incorporated into the mass on the porosity and surface property is indicated by way of example and is schematically illustrated in the accompanying drawings in which:

FIG. 1 shows an extruded strand of moist yeast, extruded without incorporation of gas according to the prior-art processes; and FIG. 2 shows a moist yeast strand extruded from the mass containing the incorporated gas according to this invention.

Figure 3:
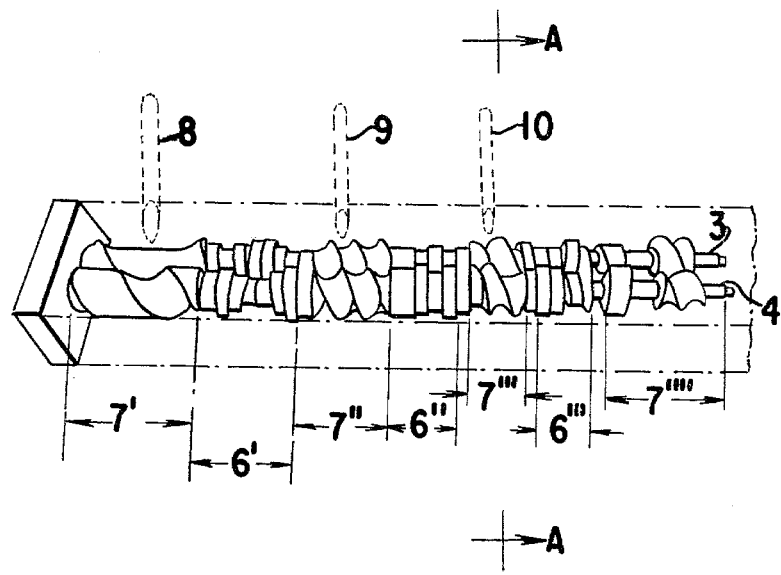
FIG. 3 shows a plan view of a mixer extruder capable of incorporating a gas.

FIG. 3 shows a plan view of a twin screw mixing and kneading extruder where the casing is indicated by dotted lines and the nozzle is not shown.

Figure 4:
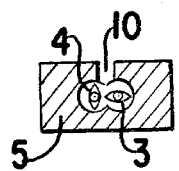
FIG. 4 shows a cross-section of FIG. 3 at the point of gas injection.

FIG. 4 shows a cross-section view along A—A of FIG. 3 showing the casing, twin mixing screws and the air inlet.

Referring to FIGS. 1 and 2, the influence of the incorporation of the preferred gas, air, on the surface appearance or porosity of the yeast granules is clearly seen from the comparison of the known yeast strands 1 shown in FIG. 1 with the porous yeast granules 2 prepared by the process embodying the present invention and shown in FIG. 2. The moist yeast extruded with air, FIG. 2, has a substantially rougher, more porous appearance and, consequently, greater surface area than the moist yeast extruded without air, FIG. 1. While the yeast strand 1, shown in FIG. 1 have relatively long sections, the yeast into which the air has been incorporated before exit from the extruder, after extrusion readily breaks into shorter particles or granules.

Apart from the fact that the yeast granule 2, shown in FIG. 2, has excellent surface properties for dehydrating and rehydrating as a result of its porosity, it readily crumbles into granules and thus special granulation procedures can be omitted in the preparation of the dormant dehydrated yeast granules, according to this invention. The particles of yeast resulting from the extrusion of the strands and the release of the contained gas are of suitable size and shape to be commercially acceptable as granules.

The extruder shown in FIGS. 3 and 4 was employed in the process. This extruder consists of twin mixing screws 3 and 4 in a twin mixing chamber 5. Each of the screws has compression zones 6 and mixing zones 7. The yeast is fed into the product input 8, and is mixed and compressed. Then the emulsifier is fed into the emulsifier inlet 9 at the beginning of the next mixing zone 7″ which is followed by a compression zone 6″. Compressed air is fed through air inlet 10 into the mixing zone 7‴ which also is followed by a compression zone 6‴, then the material under pressure is mixed in mixing zone 7″″ and extruded through extrusion nozzles (not shown).

As an example, the product input chamber of the extruder of FIGS. 3 and 4 is charged with 100 kilograms per hour of a moist yeast having a solids content of about 30% to 40%. Air equivalent at S.T.P. to about 0.2 to 0.4 volumes of the moist yeast is pumped into the chamber at an inlet 10. An emulsifier, glyceryl monostearate in an amount of 1 percent by weight of the yeast solids content, is introduced into the chamber through emulsifier inlet 9. The charge in the chamber is then mixed for about 0.1 to 1 minutes by the internal mixer to form a uniform mass which is then auger-fed to the extruder head. The extruder head is provided with nozzles each 1.0 millimeters in length and 0.5 millimeters in diameter.

The pressure and feed rate from the extruder are adjusted so that the mass is extruded from the nozzles at a rate of about 0.2 to 5 meters per second at an extruder head pressure of 5 atmospheres. The extruded strands are expressed into the ambient atmosphere so that the air included and compressed in the extruded strands is freed.

The resultant strands are coherent to the degree that they are self-supporting in lengths of about 4 to 20 diameters. These particles are suitable for granules. The resulting particles are introduced into a fluidized bed drier operating at temperatures between 40° and 110° C. The feed and exit rates of the drier are adjusted to provide a drier dwell time of about 5 to 10 minutes. The exiting particles contain about 3 to 6% of residual moisture. The particles or granules, after drying, provide the yeast in dormant state suitable for storage for commercially acceptable periods and then regeneration by the addition of water. The granules, so prepared, upon rehydration, have 95% viability, which is greater than the usual viability of presently available commercial yeast granules which average 80 to 90% viability. In addition, it is noted that the granules so prepared substantially, completely rehydrate within 10 to 30 seconds. Commercial yeast granules by the prior-art processes at the end of this time period are noted to contain unhydrated hard particles of yeast. Complete hydration of the commercial yeast requires at least 5 minutes.

The above description and example are merely illustrative of the present invention without being deemed limitative in any manner thereof.

We claim:

1. A process for the production of porous granules of compressed yeast which comprises the steps of introducing a moist yeast having a solids content of 30% to 40%, introducing from 0.2 to 2.0 times the volume of said yeast, of a gas, admixing said gas with said moist yeast to form a uniform mass, extruding said gas-yeast mass at a pressure of compression of from 1 to 10 atmospheres through orifices having a length to diameter ratio of approximately 1:1 to 4:1, allowing the escape of the gas from the interior of the extrudate to form pores communicating with the surface and recovering porous granules of compressed yeast.

2. The porous granules of compressed yeast produced by the process of claim 1.

3. The process of claim 1 wherein said gas is air.

4. The process according to claim 1 wherein said extruded porous granules of compressed yeast are dried in a single drying step in such a manner that the temperature of the yeast during the drying does not exceed 40° C.

5. The process according to claim 1 which comprises the further steps of adding an emulsifier to the moist yeast before admixing and incorporating the gas therewith.

6. The process according to claim 1 wherein said length to diameter ratio is approximately 2:1.

7. The process according to claim 1 wherein the mass is extruded from said orifice at a speed of approximately 0.2 to 4 meters per second.

8. The process according to claim 7 wherein the speed is approximately from one to two meters per second.

9. The process according to claim 1 wherein the gas is air.

10. Porous granules of active dried yeast having a total surface area formed by the outside surface of the granules plus the interior surface of pores in the granules which is at least 1.5 times the surface area formed by the outside surface of the granules, produced by the process of claim 4.

* * * * *